(12) United States Patent
Michel et al.

(10) Patent No.: US 6,440,435 B1
(45) Date of Patent: Aug. 27, 2002

(54) USE OF N-ACYLAMINO ACID COMPOUNDS AS TEXTURING AGENTS

(75) Inventors: Nelly Michel, Maisons Alfort; Christian Berger, Ecully, both of (FR)

(73) Assignee: Societe d'Exploitation de Produits pour les Industries Chimiques Seppic, Paris Cedex (FR)

( * ) Notice: Subject to any disclaimer, the term of this patent is extended or adjusted under 35 U.S.C. 154(b) by 0 days.

(21) Appl. No.: 09/845,199

(22) Filed: May 1, 2001

Related U.S. Application Data

(62) Division of application No. 09/470,516, filed on Dec. 22, 1999.

(30) Foreign Application Priority Data

Dec. 22, 1998 (FR) .............................................. 98 16239

(51) Int. Cl.⁷ ................................................. A61K 7/01
(52) U.S. Cl. ...................................................... 424/401
(58) Field of Search ......................................... 424/401

(56) References Cited

U.S. PATENT DOCUMENTS 4,016,287 A 4/1977 Eberhardt et al. .......... 424/309

FOREIGN PATENT DOCUMENTS

| DE | 2234399 | 1/1974 |
| EP | 839515 | 5/1998 |
| JP | 61291700 | 12/1986 |
| JP | 06145024 | 5/1994 |
| JP | 08337519 | 12/1996 |
| JP | 0 839 515 A2 * | 5/1998 |
| WO | WO 9221318 | 12/1992 |
| WO | WO 9809611 | 3/1998 |
| WO | WO 9904757 | 2/1999 |

* cited by examiner

*Primary Examiner*—Jose' G. Dees
*Assistant Examiner*—Konata M. George
(74) *Attorney, Agent, or Firm*—Young & Thompson

(57) ABSTRACT

Use of at least one compound of formula (I);

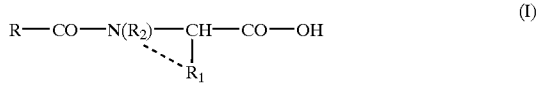

in which R represents the characterizing chain of a saturated or unsaturated, linear or branched fatty acid, comprising from 16 to 22 carbon atoms,

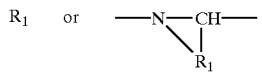

represents the characterizing chain or cyclic radical of an amino acid, $R_2$ represents a hydrogen atom or an alkyl radical comprising from 1 to 3 carbon atoms, or the topically acceptable salts thereof, as texturing agents, it being understood that the amino acid characterized by $R_1$ is not lysine, hydroxylysine or arginine. Novel compositions. Application in cosmetics.

5 Claims, No Drawings

USE OF N-ACYLAMINO ACID COMPOUNDS AS TEXTURING AGENTS

This application is a division of U.S. application Ser. No. 09/470,516, filed Dec. 22, 1999.

FIELD OF THE INVENTION

The present invention relates to a novel use of N-acylamino acid derivatives. These compounds, for example those described in the international patent applications published under the numbers WO 92/20647, WO 92/21318, WO 94/26694, WO 94/27561 and WO 98/09611, are, in particular on account of their antimicrobial and antielastic activity, used as active agents in formulations for topical use. Such cosmetic, dermopharmaceutical or pharmaceutical formulations intended to care for the skin or mucous membranes must be easy to take up with the fingers before they are applied; when they are applied on the skin or on mucous membranes, they must spread easily, penetrate quickly and melt in well while at the same time affording sensations of freshness and softness, without being perceived as greasy or oily, and, after they have been applied to the skin or mucous membranes, they must not give rise to any sheen on the skin, or any unpleasant odour, or appear sticky; however, the sensations of softness and freshness resulting from their application must remain.

SUMMARY OF THE INVENTION

Now, in order to obtain a sensory profile which satisfies a formulation, it is often necessary to include texturing agents therein, which are compounds or mixtures of compounds capable of improving the rheological and sensory properties of the formulation. The applicant has found, unexpectedly, that N-acylamino acid derivatives can be used effectively as texturing agents for cosmetic, dermopharmaceutical or pharmaceutical formulations.

Accordingly, a subject of the invention is the use of at least one compound of formula (I):

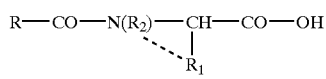

(I)

in which R represents the characterizing chain of a saturated or unsaturated, linear or branched fatty acid, the fragment R—CO comprises from 12 to 22 carbon atoms and more particularly from 16 to 22 carbon atoms, $R_1$ or 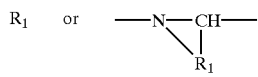

represents the characterizing chain or cyclic radical of an amino acid, $R_2$ represents a hydrogen atom or an alkyl radical comprising from 1 to 3 carbon atoms, or the topically acceptable salts thereof, as texturing agents, it being understood that the amino acid characterized by $R_1$ is not lysine, hydroxylysine or The expression "topically acceptable salt" means any salt of the acid of formula (I) which is biologically acceptable for the skin and/or mucous membranes, i.e., any salt which can in particular adjust the pH of the composition to a value of between 3 and 8 and preferably approximately equal to 5, which is a pH in the region of the skin's pH. Examples of such salts are, in particular, alkali metal salts, such as sodium, potassium or lithium salts, alkaline-earth metal salts, such as calcium, magnesium or strontium salts; they can also be metal salts such as divalent zinc, copper or manganese salts or alternatively trivalent iron, lanthanum, cerium or aluminium salts. The compound of formula (I) present in the composition which is the subject of the present invention can be in free acid form or in partially or totally salified form. The expression "characterizing chain" used in the context of the present patent application denotes the main chain of the fatty acid or of the amino acid under consideration. Thus, for a fatty acid corresponding to the general formula R—COOH, the characterizing chain will be the chain represented by R. The linear or branched, saturated or unsaturated radical R represents a radical comprising from 11 to 21 carbon atoms, chosen, for example, from undecyl, dodecyl, tridecyl, tetradecyl, pentadecyl, hexadecyl, heptadecyl, octadecyl, nonadecyl, eicosyl, uneicosyl, docosyl, heptadecenyl, eicosenyl, uneicosenyl and heptadecadienyl radicals.

A subject of the invention is, more particularly, the use as defined above, for which, in formula (I), the fragment R—CO represents in particular one of the following radicals: dodecanoyl (lauroyl), tetradecanoyl (myristyl), hexadecanoyl (palmitoyl), octadecanoyl (stearyl), eicosanoyl (arachidoyl), docosanoyl (behenoyl), octadecenoyl (oleyl), eicosenoyl (gadoloyl), docosenoyl (erucyl) or octadecadienoyl (linolenoyl). For an amino acid represented by the general formula;

$HN(R_2)$—$CHR_1$—$COOH$, it will be characterized by the definition of $R_1$; for an amino acid represented by the general formula:

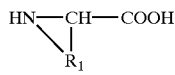

it will be characterized by the definition of the cyclic radical:

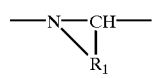

In the context of the present invention, the chain or the cyclic radical characterizing the amino acid are chosen from those of glycine, alanine, serine, aspartic acid, glutamic acid, valine, threonine, proline, leucine, phenylalanine, isoleucine, histidine, tyrosine, tryptophan, asparagine, cysteine, cystine, methionine, hydroxyproline, ornithine and sarcosine. A subject of the invention is, more particularly, the use as described above for which, in formula (I), the chain or the cyclic radical characterizing the amino acid are chosen from those of glycine, proline, glutamic acid and sarcosine.

The expression "at least one compound of formula (I)" means that the invention can be carried out with one or more of these compounds. The expression "or more of these compounds" means:

either a mixture of compounds of formula (I), resulting from the condensation of a single amino acid with a mixture of fatty acids, and more particularly a mixture of fatty acids of natural origin, or a mixture of compounds of formula (I) resulting from the condensation of a mixture of amino acids with a single fatty acid, or a mixture of compounds of formula (I) resulting from the condensation of a mixture of amino *acids with a mixture of fatty acids, and more particularly with a mixture of fatty acids of natural origin. The mixtures of fatty acids of natural origin which can be used advantageously for the preparation of the compounds of formula (I) are, in particular, those derived from coconut oil, palm kernel oil, palm oil, soybean oil, rapeseed oil, bovine tallow, spermaceti oil, herring oil or castor oil.

According to a very specific aspect of the present invention, its subject is the use, as described above, of a mixture comprising at least one compound of formula (Ia) corresponding to formula (I), in which the cyclic radical characterizing the amino acid is that of praline, and at least one compound of formula (Ib) corresponding to formula (I) in which the characterizing chain of the amino acid is that of glutamic acid, and optionally at least one compound of formula (Ic) corresponding to formula (I) in which $R_2$ represents a methyl radical and $R_1$ represents the characterizing chain of sarcosine; as an example of such a use, mention may be made of the use of the mixture comprising N-palmitoylproline and N-palmitoylglutamic acid or the sodium or magnesium salts thereof or the use of the mixture comprising N-palmitoylproline, N-palmitoylglutamic acid and N-palmitoylsarcosine or the sodium or magnesium salts thereof.

According to another very specific aspect of the present invention, its subject is the use, as described above, of a composition comprising N-cocoylglycine or one of the topically acceptable salts thereof.

The compounds of formula (I) are obtained by the methods known to those skilled in the art and described in particular in the international patent applications published under the numbers WO 92/20647, WO 92/21318, WO 94/26694, WO 94/27561 and WO 98109611.

A subject of the invention is also a composition (A) comprising;

a) from 10% to 95% by weight, and more particularly from 60% to 80% by weight, of at least one compound of formula (I):

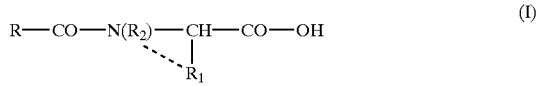

in which R represents the characterizing chain of a saturated or unsaturated, linear or branched fatty acid comprising from 12 to 22 carbon atoms, $R_1$ or 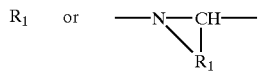

represents the chain or the cyclic radical characterizing the amino acid, chosen from those of glycine, alanine, serine, aspartic acid, glutamic acid, valine, threonine, proline, leucine, phenylalanine, isoleucine, histidine, tyrosine, tryptophan, asparagine, cysteine, cystine, methionine, hydroxyproline, ornithine and sarcosine, R, represents a hydrogen atom or an alkyl radical comprising from 1 to 3 carbon atoms, or one of the topically acceptable salts thereof, and $R_2$ represents a hydrogen atom or an alkyl radical comprising from 1 to 3 carbon atoms, or one of the topically acceptable salts thereof, and b) from 90% to 5% by weight of at least one compound of formula (II)

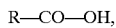

or one of the topically acceptable salts thereof.

A subject of the invention is, more particularly, a composition (A) as defined above, for which the radical R comprises from 16 to 22 carbon atoms, and more particularly from 16 to 18 carbon atoms. According to one very specific aspect of the present invention, its subject is the composition (A) as defined above, comprising:

from 30% to 50% by weight of palmitoylproline,
from 5% to 25% by weight of N-palmitoylglutamic acid,
from 0% to 25% by weight of N-palmitoylsarcosine and
from about 5% to about 40% by weight of palmitic acid.

According to another very specific aspect of the present invention, its subject is the composition (A) as defined above, comprising:

from 30% to 70% by weight of cocoylglycine,
from 0% to 25% by weight of N-cocoylsarcosine and
from about 5% to about 45% by weight, and more particularly from 5% to about 20% by weight, of the mixture of fatty acids derived from coconut oil.

A subject of the present invention is also a cosmetic, dermopharmaceutical or pharmaceutical formulation comprising, as texturing agent, an effective amount of at least one compound of formula I as defined above. In the context of the present invention, the expression "effective amount" means an amount representing from about 0.1% to about 5% by weight of the formulation.

The cosmetic formulation is usually in the form of an aqueous solution, a dilute alcoholic solution or a simple or multiple emulsion, such as a water-in-oil (W/O), oil-in-water (O/W) or water-in-oil-in-water (W/O/W) emulsion, or a dispersion of liposomes or of aminosomes. The term "aminosome" denotes a type of liposome formed by amphiphilic amino acid derivatives. Examples which may be mentioned are creams, milks, lotions, antisun emulsions, cosmetic wipes, gels such as shower gels or cream-gels, oils, soaps, liquid soaps, syndets, intimate-hygiene products, shampoos, make-up powders and mascaras.

A subject of the invention is also the use of a composition (A) as defined above, to prepare a cosmetic, dermopharmaceutical or pharmaceutical formulation. This formulation is prepared according to the methods known to those skilled in the art which are suitable for the desired type of formulation, by combining composition (A) with the usual cosmetic active agents and excipients.

The compounds of formula (I) are compatible with most known excipients, whether this is, for example, with reverse latices such as the compounds sold under the names Sepigel™ 305, sepigel™ 501, Sepigel™ 502, Simulgel™ 600, SiMulgel™ A or Simulgel™ EG, or with the compositions sold under the names Montanov™ 68, Montanov™ 14, Montanov™ 82, Montanov™ 202 or Sepigel™ N and described, for example, in the patent applications published under the numbers WO 92/02778, WO 95/13863, WO 96/37285, WO 98/22207 or WO 98/47610.

The examples which follow illustrate the invention without, however, limiting it.

DETAILED DESCRIPTION OF THE INVENTION

EXAMPLE 1

Sensory Profile of Composition According to the Invention a) A composition comprising about 45% of palmitoylproline, from 10% to 15% of N-palmitoylglutamic acid, from 10% to 15% of N-palmitoylsarcosine and about 30% of palmitic acid is prepared.

b) A cream-gel (I) is prepared containing, as texturing agent, 3% of the composition prepared in paragraph a) and, as thickener, 3.5% of Sepigel™ 305, and a cream-gel (II) containing, as thickener, 3.5% of Sepigel™ 305 and containing no texturing agent.

c) The sensory test was carried out on a panel of 15 individuals; these individuals assessed and compared the qualities of the two cream-gels in the following three situations:

1) Assessment of the Uptake of the Cream-gel with the Fingers in Order Subsequently to Spread it on the Skin The panel assessed the ease of uptake.

2) Assessment of the Application of the Cream-gel onto the Skin

The panel assessed the ease of spreading, the melting nature, the sensation of freshness, the softness of the product, the absence of a greasy sensation of the product and the speed of penetration.

3) Assessment After Application

The panel assessed the odour on the skin, the sheen of the skin, the sticky aspect on the skin, the softness of the skin and the presence of residue.

The results are given in the table below in the following manner:

positive assessments or negative assessments when at least two thirds of the members are of the same opinion:

undifferentiated assessment (indicated by "idem") when less than two thirds of the members are of the same opinion:

|  | Cream-gel (I) Invention | Cream-gel (II) Comparison |
|---|---|---|
| Ease of uptake | Easier | Less easy |
| Ease of spreading | Easier | Less easy |
| Melting nature | Melts more easily | Melts less easily |
| Sensation of freshness | Melts more easily | " |
| Softness | Softer | Less soft |
| Greasy sensation | Less greasy | More greasy |
| Penetration | Faster | Slower |
| Odour on the skin | " | " |
| Sheen of the skin | Less shiny | More shiny |
| Stickiness on the skin | " | " |
| Softness of the skin | Softer | Less soft |
| Persistence | More persistent | Less persistent |

These results show that the presence of compounds of formula (I) in a cosmetic formulation markedly improve the sensory profile of the said formulation by improving its tactile properties.

Examples of Cosmetic Formulations

EXAMPLES 2 TO 37

The cosmetic formulations below were prepared using the composition prepared in paragraph a) of Example 1 (referred to hereinbelow as composition A):

EXAMPLE 2

Care Cream

| Cyclomethicone: | 10% |
|---|---|
| Composition A: | 3% |
| Sepigel ® 502: | 0.8% |
| Montanov ® 68: | 2% |
| Stearyl alcohol: | 1.5% |
| Preserving agent: | 0.65% |
| Lysine: | 0.025% |
| EDTA (disodium salt): | 0.05% |
| Xanthan gum: | 0.2% |
| Glycerol: | 3% |
| Water: | qs 100% |

EXAMPLE 3

Care Cream

| Cyclomethicone: | 10% |
|---|---|
| Composition A: | 3% |
| Sepigel ® 502: | 0.8% |
| Montanov ® 68: | 2% |
| Perfluoropolymethyl isopropyl ether: | 0.5% |
| Stearyl alcohol: | 1.5% |
| Preserving agent: | 0.65% |
| Lysine: | 0.025% |
| EDTA (disodium salt): | 0.05% |
| Pemulen ® TR: | 0.2% |
| Glycerol: | 3% |
| Water: | qs 100% |

EXAMPLE 4

After-shave Balm

| FORMULA | | |
|---|---|---|
| A | Composition A: | 3% |
|  | Sepigel ™ 502: | 1.5% |
|  | Water: | qs 100% |
| B | Micropearl ™ 100: | 5.0% |
|  | Sepicide ™ CI: | 0.50% |
|  | Fragrance: | 0.20% |
|  | 95° ethanol: | 10.0% |
| PROCEDURE | | |
| Add B to A. | | |

EXAMPLE 5

Satin Emulsion for the Body

| FORMULA | | |
|---|---|---|
| A | Simulsol ™ 165: | 5.0% |
|  | Lanol ™ 1688: | 8.50% |
|  | Karite butter: | 2% |
|  | Liquid paraffin: | 6.5% |
|  | Lanol ™ 14M: | 3% |
|  | Lanol ™ S: | 0.6% |
|  | Water: | 66.2% |
| C | Micropearl ™ M 100: | 5% |
| D | Composition A: | 3% |
|  | Sepigel ™ 502: | 3% |
| E | Sepicide ™ CI: | 0.3% |
|  | Sepicide ™ HB: | 0.5% |

| FORMULA | | |
|---|---|---|
| | Monteine ™ CA: | 1% |
| | Fragrance: | 0.20% |
| | Vitamin E acetate: | 0.20% |
| | Sodium pyrrolidone-carboxylate: | 1% (moisturizer) |

Procedure

Add C to B, emulsify a in A at 70° C. and then add D at 60° C., followed by E at 30° C.

EXAMPLE 6
Body Milk

| FORMULA | | |
|---|---|---|
| A | Simulsol ™ 165: | 5.0% |
| | Lanol ™ 1688: | 12.0% |
| | Lanol ™ 14M: | 2.0% |
| | Cetyl alcohol: | 0.3% |
| | Schercemol ™ OP: | 3% |
| B | Water: | 100% |
| C | Composition A: | 3% |
| | Sepigel ™ 502: | 0.35% |
| D | Sepicide ™ CI: | 0.2% |
| | Sepicide ™ HB: | 0.5% |
| | Fragrance: | 0.20% |

Procedure

Emulsify B in A at about 75° C.; add C at about 60° C., followed by D at about 30° C.

EXAMPLE 7
O/W Cream

| FORMULA | | |
|---|---|---|
| A | Simulsol ™ 165: | 5.0% |
| | Lanol ™ 1688: | 20.0% |
| | Lanol ™ P: | 1.0% |
| B | Water | qs 100% |
| C | Composition A: | 3% |
| | Sepigel ™ 502; | 2.5% |
| D | Sepicide ™ CI: | 0.20% |
| | Sepicide ™ HB: | 0.30% |

Procedure

Introduce B into A at about 75° C.; add C at about 60° C., followed by D at about 45° C.

EXAMPLE 8
Non-greasy Antisun Gel

| FORMULA | | |
|---|---|---|
| A | Composition A: | 3% |
| | Sepigel ™ 502: | 0.8% |
| | Water: | 30% |
| B | Sepicide ™ CI: | 0.20% |
| | Speicide ™ HB: | 0.30% |
| | Fragrance: | 0.10% |
| C | Dye: | qs |
| | Water: | 30% |

| FORMULA | | |
|---|---|---|
| D | Micropearl ™ M 100: | 3.00% |
| | Water: | qs 100% |
| E | Silicone oil: | 2.0% |
| | Parsol ™ MCX: | 5.00% |

Procedure

Introduce B into A; add C, then D and then E.

EXAMPLE 9
Antisun Milk

| FORMULA | | |
|---|---|---|
| A | Sepiperl ™ N: | 3.0% |
| | Sesame oil: | 5.0% |
| | Parsol ™ MCX: | 5.0% |
| | λ-Carrageenan: | 0.10% |
| B | Water: | qs 100% |
| C | Composition A: | 3% |
| | Sepigel ™ 502: | 0.8% |
| D | Fragrance: | qs |
| | Preserving agent: | qs |

Procedure

Emulsify B in A at 75° C., then add C at about 60° C., followed by D at about 30° C. and adjust the pH if necessary.

EXAMPLE 10
Massage Gel

| FORMULA | | |
|---|---|---|
| A | Composition A: | 3% |
| | Sepigel ™ 501: | 3.5% |
| | Water: | 20.0% |
| B | Dye: | 2 drops/100 g |
| | Water: | qs |
| C | Alcohol: | 10% |
| | Menthol: | 0.10% |
| D | Silicone oil: | 5.0% |

Procedure

Add B to A; then add C to the mixture, followed by D.

EXAMPLE 11
Massage Care Gel

| FORMULA | | |
|---|---|---|
| A | Composition A: | 3% |
| | Sepigel ™ 502: | 3.0% |
| | Water: | 30% |
| B | Sepicide ™ CI: | 0.20% |
| | Sepicide ™ HB: | 0.30% |
| | Fragrance: | 0.05% |
| C | Dye: | qs |
| | Water: | qs 100% |
| D | Micropearl ™ SQL: | 5.00% |
| | Lanol ™ 1688: | 2% |

Procedure
    Prepare A; add B, then C and then D.

EXAMPLE 12
Sunburn Gel

| | FORMULA | | |
|---|---|---|---|
| A | Composition A: | 3% |
| | Sepigel ™ 502: | 4% |
| | Water: | 30% |
| B | Elastine HPM: | 5.0% |
| C | Micropearl ™ M 100: | 3% |
| | Water | 5% |
| D | Sepicide ™ CI: | 0.2% |
| | Sepicide ™ HB: | 0.3% |
| | Fragrance: | 0.06% |
| | 50% sodium pyrrolidonecarboxylate: | 1% |
| | Water: | qs 100% |

Procedure
    Prepare A; add B. then C and then D.

EXAMPLE 13
Body Milk

| | FORMULA | | |
|---|---|---|---|
| A | Sepiperl ™ N: | 3.0% |
| | Glyceryl triheptonate: | 10.0% |
| | Water: | qs 100% |
| C | Composition A: | 1.5% |
| | Sepigel ™ 502: | 1.0% |
| D | Fragrance: | qs |
| | Preserving agent: | qs |

Procedure
    Melt A at about 75° C. Emulsify B in A at 75° C. and then add C at about 60° C., followed by D.

EXAMPLE 14
Maka-up-removing Emulsion Containing Sweet Almond Oil

| FORMULA | |
|---|---|
| Montanov ™ 68: | 5% |
| Sweet almond oil: | 5% |
| Water: | qs 100% |
| Composition A: | 1% |
| Sepigel ™ 502: | 0.3% |
| Glycerol: | 5% |
| Preserving agent: | 0.2% |
| Fragrance: | 0.3% |

EXAMPLE 15
Moisturizing Cream for Greasy Skin

| FORMULA | |
|---|---|
| Montanov ™ 68: | 5% |
| Cetylstearyl octanoate: | 8% |
| Octyl palmitate: | 2% |
| Water: | qs 100% |
| Composition A: | 2% |
| Sepigel ™ 502: | 0.6% |
| Micropearl ™ M100: | 3.0% |
| Mucopolysaccharides: | 5% |
| Sepicide ™ HB: | 0.8% |
| Fragrance: | 0.3% |

EXAMPLE 16
Alcohol-free Soothing After-shave Balm

| FORMULA | |
|---|---|
| Lanol ™ 99: | 2% |
| Sweet almond oil: | 0.5% |
| Water: | qs 100% |
| Composition A: | 3% |
| Sepigel ™ 501: | 3% |
| Sepicide ™ XB: | 0.3% |
| Sepicide ™ CI: | 0.2% |
| Fragrance: | 0.4% |

EXAMPLE 17
Cream Containing HAAs for Sensitive Skin

| FORMULA | |
|---|---|
| Lanol ™ 99: | 2% |
| Montanov ™ 68: | 5.0% |
| Water: | qs 100% |
| Composition A: | 0.1 to 5% |
| Sepigel ™ 501: | 1.5% |
| Gluconic acid: | 1.50% |
| Triethylamine: | 0.9% |
| Sepicide ™ HB: | 0.3% |
| Sepicide ™ CI: | 0.2% |
| Fragrance: | 0.4% |

EXAMPLE 18
After-sun Soothing Care Product

| FORMULA | |
|---|---|
| Lanol ™ 99: | 10.0% |
| Water: | qs 100% |
| Composition A: | 3% |
| Sepigel ™ 502: | 2.5% |
| Sepicide ™ HB: | 0.3% |
| Sepicide ™ CI: | 0.2% |
| Fragrance | 0.4% |
| Dye: | 0.03% |

EXAMPLE 19
Make-up-Removing Milk

| FORMULA | |
|---|---|
| Sepiperl ™ N: | 3% |
| Primol ™ 352: | 8.0% |
| Sweet almond oil: | 3% |

-continued

| FORMULA | |
|---|---|
| Water: | qs 100% |
| Composition A: | 2% |
| Sepigel ™ 502: | 0.8% |
| Preserving agent: | 0.2% |

EXAMPLE 20
Body Milk

| FORMULA | |
|---|---|
| Sepiperl ™ N: | 3.5% |
| Lanol ™ 37T: | 8.0% |
| Solagum ™ L: | 0.05% |
| Water: | qs 100% |
| Benzophenone: | 2.0% |
| Dimethicone 350 cPs: | 0.05% |
| Composition A: | 2% |
| Sepigel ™ 502: | 0.8% |
| Preserving agent: | 0.2% |
| Fragrance: | 0.4% |

EXAMPLE 21
Liquid Emulsion at Alkaline pH

| | |
|---|---|
| Marcol ™ 82: | 5.0% |
| NaOH: | 10.0% |
| Water: | qs 100% |
| Composition A: | 4% |
| Sepigel ™ 502: | 1.5% |

EXAMPLE 22
Liquid Foundation

| FORMULA | |
|---|---|
| Simulsol ™ 165: | 5.0% |
| Lanol ™ 84D: | 8.0% |
| Lanol ™ 99: | 5.0% |
| Water: | qs 100% |
| Mineral pigments and fillers: | 10.0% |
| Composition A: | 3% |
| Sepigel ™ 502: | 1.2% |
| Preserving agent: | 0.2% |
| Fragrance: | 0.4% |

EXAMPLE 23
Antisun Milk

| FORMULA | |
|---|---|
| Sepiperl ™ N: | 3.5% |
| Lanol ™ 37T: | 10.0% |
| Parsol NOX ™: | 5.0% |
| Eusolex ™ 4360: | 2.0% |
| Water: | qs 100% |
| Composition A: | 3% |
| Sepigel ™ 502: | 1.8% |

-continued

| FORMULA | |
|---|---|
| Preserving agent: | 0.2% |
| Fragrance: | 0.4% |

EXAMPLE 24
Gel for the Contour of the Eyes

| FORMULA | |
|---|---|
| Composition A: | 1% |
| Sepigel ™ 502: | 2% |
| Fragrance | 0.06% |
| Sodium pyrrolidonecarboxylate: | 0.2% |
| Dow Corning ™ 245 fluid: | 2.0% |
| Water: | qs 100% |

EXAMPLE 25
Leave-on Care Composition

| FORMULA | |
|---|---|
| Composition A: | 3% |
| Sepigel ™ 502: | 1.5% |
| Fragrance: | qs |
| Preserving agent: | qs |
| Dow Corning ™ X2 8360: | 5.0% |
| Dow Corning ™ Q2 1401: | 15% |
| Water: | qs 100% |

EXAMPLE 26
Slendering Gel

| | |
|---|---|
| Composition A: | 5% |
| Sepigel ™ 501: | 5% |
| Ethanol: | 30% |
| Menthol: | 0.1% |
| Caffeine: | 2.5% |
| Extract of Ruscus: | 2% |
| Extract of English ivy: | 2% |
| Sepicide ™ HP: | 1% |
| Water: | qs 100% |

EXAMPLE 27
Comfort Cream for Sensitive Skin

| | |
|---|---|
| Composition A: | 3% |
| Sepigel ™ 305: | 2% |
| Lipacid ™ C8G: | 0.5% |
| Montanov ™ 202: | 0.3% |
| Phytosqualane: | 5% |
| Cyclomethicone/polymethyl cyclosiloxane: | 10% |
| Sepicide ™ HB: | 0.2% |
| Water: | qs 100% |

EXAMPLE 28
Soothing Care Product

| | |
|---|---|
| Composition A: | 3% |
| Sepigel ™ 305: | 0.7% |
| Simulsol ™ 165: | 5% |
| Capric caprylic triglyceride: | 5% |
| Sepicide ™ HB: | 0.3% |
| Sepicide ™ CI: | 0.2% |
| Water: | qs 100% |

EXAMPLE 29
Cream-gel for Sensitive Skin

| | |
|---|---|
| Composition A: | 3% |
| Simulgel ™ 600: | 2% |
| Isohexadecane | 5% |
| Borage oil: | 1% |
| Sepicide ™ HB: | 0.3% |
| Sepicide ™ CI: | 0.2% |
| Fragrance: | 0.1% |
| Water: | qs 100% |

EXAMPLE 30
After-sun Soothing Care Product

| | |
|---|---|
| Composition A: | 3% |
| Sepigel ™ 502: | 4% |
| Cyclomethicone and dimethiconol: | 5% |
| Lanol ™ 189: | 5% |
| Sepicide ™ HS: | 0.3% |
| Sepicide ™ CI: | 0.2% |
| Fragrance: | 0.1% |
| Water: | qs 100% |

EXAMPLE 31
Soothing Gel for the Hands

| | |
|---|---|
| Composition A: | 3% |
| Sepigel ™ 305: | 4% |
| Isostearyl isostearate: | 5% |
| Micropearl ™ M305: | 1% |
| Glycerol: | 10% |
| Sepicide ™ HB: | 0.3% |
| Sepicide ™ CI: | 0.2% |
| Fragrance: | 0.2% |
| Water: | qs 100% |

EXAMPLE 32
Moisturizing Cream for Sensitive Skin

| | |
|---|---|
| Montanov ™ 68: | 7% |
| Isostearyl isostearate: | 5% |
| Dimethicone: | 10% |
| Water: | qs 100% |
| Composition A: | 2% |
| Sepigel ™ 305: | 1% |
| Sepicide ™ HB: | 0.3% |
| Sepicide ™ CI: | 0.2% |
| Fragrance: | 0.2% |

EXAMPLE 33
Self-tanning Care Product

| | |
|---|---|
| Composition A: | 3% |
| DHA: | 1% |
| Sepigel ™ 305: | 2% |
| Montanov ™ 202: | 3% |
| Sweet almond oil: | 7% |
| Dimethicone: | 3% |
| Fragrance | 0.1% |
| Sepifilm ™ HB: | 0.3% |
| Sepifilm ™ CI: | 0.2% |
| Water | qs 100% |

EXAMPLE 34
Compact Powder

| | |
|---|---|
| Talc: | 57% |
| Polymethylenemethacrylate: | 15% |
| Dimethicone: | 15% |
| Zinc stearate: | 5% |
| Isononylisononanoate: | 5% |
| Composition A: | 3% |
| Colorants: | qs |

EXAMPLE 35
Cream Gel

| | FORMULA | |
|---|---|---|
| A | Water: | 10% |
| | Butylene glycol: | 4% |
| | PEG-400: | 4% |
| | Titanium dioxide: | 2% |
| | Yellow iron oxide: | 0.8% |
| | Red iron oxide: | 0.3% |
| | Black iron oxide: | 0.05% |
| | Pecosil ™ PS100: | 1.5% |
| B | Isononyl isononanoate: | 4% |
| | Caprylic capric triglyceride: | 4% |
| | Composition A: | 1% |
| | Simulgel ™ A: | 3% |
| | Cyclomethicone: | 4% |
| C | Water: | qs 100% |
| | Micropearl ™ M305: | 2% |
| | Tetrasodium EDTA: | 0.05% |
| D | Sepicide ™ HB: | 0.3% |
| | Sepicide ™ CI: | 0.2% |
| | Fragrance: | 0.2% |

Procedure

Mix together B and C to form the gel. Add A, followed by D.

Properties

Appearance: fluid cream; pH=7;

Viscosity 15,000 mPa.s (Brookfield LV M3, 6 rpm)

EXAMPLE 36
Anti-wrinkle Complex

| FORMULA | | |
|---|---|---|
| A | Water: | 10% |
| | Butylene glycol: | 4% |
| | PEG-400: | 4% |
| | Titanium dioxide: | 2% |
| | Yellow iron oxide: | 0.8% |
| | Red iron oxide: | 0.3% |
| | Black iron oxide: | 0.05% |
| | Proteol ™ Oat: | 1.5% |
| B | Isononyl isononanoate: | 4% |
| | Caprylic/capric triglycerride: | 4% |
| | Composition A: | 1% |
| | Simulgel ™ A: | 3% |
| | Cyclomethicone: | 4% |
| C | Water: | qs 100% |
| | Micropearl ™ M305: | 2% |
| | Tetrasodium EDTA: | 0.05% |
| D | Sepicide ™ HB: | 0.3% |
| | Sepicide ™ CI: | 0.2% |
| | Fragrance: | 0.2% |

Procedure

Mix together B and C to form the gel. Add A, followed by D.

Properties

Appearance: cream; pH=7.2;

Viscosity 35,200 mPa.s (Brookfield LV M4, 6 rpm)

EXAMPLE 37
Matt-effect Emulsion

| FORMULA | | |
|---|---|---|
| A | Composition A: | 0.5% |
| | Simugel ™ EG: | 1% |
| | Dimethicone: | 5% |
| B | Water: | qs 100% |
| | Micropearl ™ M305: | 10% |
| | Butylene glycol: | 5% |
| C | Sepicide ™ HB: | 0.5% |
| | Fragrance: | 0.2% |

Procedure

Mix together A and B to form the gel, Add C.

Properties

Appearance: fluid formula; pH=5.7

Visscosity 4700 mPa.s (Brookfield LV M3, 6 rpm)

The commercial names given above have the following definitions:

Montanov™ 68 (cetearyl glucoside) is a self-emulsifying composition as described in WO 92/06778, sold by the company SEPPIC.

Sepigel™ 502 is a thickener based on acrylamide copolymers, sold by the company SEPPIC.

Pemulen™ TR is an acrylic polymer sold by Goodrich.

Micropearl™ M 100 is an ultrafine powder which feels very soft and has a matt effect, sold by the company Matsumo, Sepicide™ CI, imidazolineurea, is a preserving agent sold by the company SEPPIC.

Simulsol™ 165 (glyceryl stearate/PEG-100 stearate) is a self-emulsifying composition sold by the company SEPPIC.

Lanol™ 1688 is an emollient ester with a non-greasy effect, sold by the company SEPPIC.

Lanol™ 14M and Lanoim S are consistency factors sold by the company SEPPIC.

Sepicide™ HB, which is a mixture of phenoxyethanol, methyl paraben, ethyl paraben, propyl paraben and butyl paraben, is a preserving agent sold by the company SEPPIC.

Monteine™ CA is a moisturizer sold by the company SEPPIC.

Schercemol™ OP is an emollient ester with a non-greasy effect.

Lanol™ P is an additive with a stabilizing effect, sold by the company SEPPIC.

Parsol™ MCX is octyl para-methoxycinnamate, sold by the company Givaudan.

Sepiperl™ N is a nacreous agent sold by the company SEPPIC, based on a mixture of alkyl polyglucosides such as those described in WO 95/138063.

Micropearl™ SOL is a mixture of microparticles containing squalane which is released under the action of massaging; it is sold by the company Matsumo.

Lanol™ 99 is isononyl isononanoater sold by the company SEPPIC.

Lanol™ 37T is glyceryl triheptanoate, sold by the company SEPPIC.

Solagum™ L is a carrageenan sold by the company SEPPIC.

Marcol™ 82 is a liquid paraffin sold by the company Esso.

Lanol™ 84D is dioctyl malate, sold by the company SEPPIC.

Parsol NOX™ and Eusolex™ 4360 are two sunscreens sold by the companies Givaudan and Merck, respectively.

Dow Corning™ 245 fluid is cyclomethicone, sold by the company Dow Corning.

Montanov™ 202 (arachidyl glucoside/behenyl alcohol) is a self-emulsifying composition as described in WO 92/06778, sold by the company SEPPIC.

Lipacid™ C8G (octanoylglycine) is sold by the company SEPPIC.

Proteal™ Oat is a mixture of N-lauroyl (oligo)amino acids obtained from oat protein.

Simulgel™ 600 is a thickener based on acrylamide copolymers, sold by the company SEPPIC.

Lanol™ 189 is an ester with a rich, creamy feel, sold by the company SEPPIC.

Micropearl™ M305 is a crosslinked polymethyl methacrylate copolymer sold by the company Matsumo; it gives a matt appearance when it is used in large amount (about 10%).

Simulgel™ M EG is an emulsifying thickener in the form of a reverse latex based on a copolymer of sodium acrylate and sodium acryloyldimethyltaurate in isohexadecane with sorbitan oleate, sold by the company SEPPIC.

Simulgel™ A is a thickener in the form of a reverse latex based on neutralized acrylic acid homopolymer in isohexadecane with 40E0 ethoxylated castor oil, sold by the company SEPPIC.

Pecosil™ PS100 is a dimethicone copolyol phosphate sold by the company Phoenix.

We claim:

1. The method of improving the texture of a cosmetic, dermocosmetic or pharmaceutical formulation, which comprises combining at least one cosmetic agent and at least one excipient with an effective amount of a texturing composition; said texturing composition comprising N-cocoyl glycine or one of a topically acceptable salt thereof; said effective amount representing from about 0.1% to about 5% by weight of the formulation.

2. The method according to claim 1, wherein the composition comprises from 30% to 70% by weight of N-cocoyl glycine, from 0% to 25% by weight of N-cocoyl sarcosine and from 5% to 45% by weight of a mixture of fatty acids derived from coconut oil.

3. The method according to claim 2, wherein the composition comprises from 5% to 20% by weight of the mixture of fatty acids derived from coconut oil.

4. A cosmetic, dermocosmetic or pharmaceutical formulation comprising as a texturing agent from about 0.1% to about 5% by weight of a composition comprising from 30% to 70% by weight of N-cocoyl glycine, from 0% to 25% by weight of N-cocoyl sarcosine and from 5% to 45% by weight of a mixture of fatty acids derived from coconut oil.

5. The formulation according to claim 4, wherein the composition comprises from 5% to 20% by weight of the mixture of fatty acids derived from coconut oil.

* * * * *